(12) United States Patent
Kleinerman (10) Patent No.: US 6,840,669 B2
(45) Date of Patent: *Jan. 11, 2005

(54) METHODS AND DEVICES FOR SENSING TEMPERATURE AND ANOTHER PHYSICAL PARAMETER WITH A SINGLE OPTICAL PROBE

(76) Inventor: Marcos Y. Kleinerman, 215 Sunset Ave., Amherst, MA (US) 01002

( * ) Notice: Subject to any disclaimer, the term of this patent is extended or adjusted under 35 U.S.C. 154(b) by 0 days.

This patent is subject to a terminal disclaimer.

(21) Appl. No.: 10/643,700

(22) Filed: Aug. 18, 2003

(65) Prior Publication Data

US 2004/0156419 A1 Aug. 12, 2004

Related U.S. Application Data

(63) Continuation-in-part of application No. 10/251,416, filed on Sep. 20, 2002, now Pat. No. 6,607,300.

(51) Int. Cl.[7] .............................. G01J 1/20; G01J 1/42; G01N 21/64; G01N 7/00
(52) U.S. Cl. ...................... 374/120; 374/121; 374/131; 250/483.1; 250/484.3; 436/136; 422/82.05; 422/82.13; 422/83
(58) Field of Search ................................ 374/120, 121, 374/131, 161, 130; 250/483.1, 484.3, 459.1, 461.1; 436/136, 68, 172, 164; 422/82.05, 82.13, 83

(56) References Cited

U.S. PATENT DOCUMENTS

| | | | | |
|---|---|---|---|---|
| 4,374,328 A | * | 2/1983 | Tekippe et al. | ......... 250/458.1 |
| 4,569,570 A | * | 2/1986 | Brogardh et al. | ............. 385/12 |
| 4,708,494 A | * | 11/1987 | Kleinerman | ................ 374/161 |
| 4,729,668 A | * | 3/1988 | Angel et al. | ................ 374/161 |
| 5,302,025 A | * | 4/1994 | Kleinerman | ................ 374/131 |
| 5,304,809 A | * | 4/1994 | Wickersheim | ........... 250/458.1 |
| 5,332,316 A | * | 7/1994 | Kleinerman | ................ 374/161 |
| 5,499,313 A | * | 3/1996 | Kleinerman | ................ 385/123 |
| 5,991,479 A | * | 11/1999 | Kleinerman | ................ 385/31 |
| 6,515,289 B1 | * | 2/2003 | Kask | ....................... 250/459.1 |
| 6,648,506 B2 | * | 11/2003 | McGrath et al. | ............ 374/161 |
| 6,664,111 B2 | * | 12/2003 | Bentsen et al. | ............... 436/68 |
| 2002/0158212 A1 | * | 10/2002 | French et al. | ............ 250/459.1 |
| 2003/0128737 A1 | * | 7/2003 | McGrath et al. | ............ 374/161 |

* cited by examiner

*Primary Examiner*—Gail Verbitsky (57) ABSTRACT

Optical methods and devices for measuring temperature and a second physical parameter, using a single photoluminescent probe material comprised of a single luminophor, and methods and devices for determining temperature-corrected values of said second physical parameter, which can be an oxygen or air pressure or a parameter chosen from the group comprising an electrical current, a magnetic field and an electrical field or voltage. The luminophor is excited sequentially by a first excitation light of chosen first wavelengths and intensity $P_1$ which generates a first luminescence light of intensity $I_1$, and a second excitation light of chosen second wavelengths and intensity $P_2$ which generates a second luminescence light of intensity $I_2$. The ratio $(I_2.P_1/I_1.P_2)$ varies substantially in a known manner with varying temperature, substantially independent of the magnitude of said second physical parameter, thus providing a temperature correction factor to the measurement of said second physical parameter.

16 Claims, 4 Drawing Sheets

FIG. 1

THERMALLY ACTIVATED FLUORESCENCE INTENSITY $I_f$ VS. INVERSE ABSOLUTE TEMPERATURE OF DMSO SOLUTIONS OF RHODAMINE 6G AND TWO OTHER DYES

EFFECT OF A MAGNETIC FIELD OF 14.6 TESLA ON THE TRANSMISSION SPECTRA OF A Nd-DOPED Ba CROWN GLASS, FOR THE $^4I_{9/2} \rightarrow {}^4F_{5/2}$ TRANSITION

FIG. 4

METHODS AND DEVICES FOR SENSING TEMPERATURE AND ANOTHER PHYSICAL PARAMETER WITH A SINGLE OPTICAL PROBE

CROSS-REFERENCE TO RELATED APPLICATIONS

This application is a Continuation in Part of application Ser. No. 10/251,416 filed Sep. 20, 2002 now U.S. Pat. No. 6,607,300.

FIELD OF THE INVENTION

The present invention relates to methods and devices for the measurement of temperatures and other physical parameters using a single optical fiber or other probe, and more particularly to said methods and devices using photoluminescent probes. The invention is applicable to physical parameters regardless of whether said parameters affect the position of the photoluminescent energy levels of said probes.

BACKGROUND

The quantitative measurements of a plurality of physical variables like pressure, electric or magnetic field, or concentrations of chemical analytes are usually affected by temperature variations. In order to provide temperature corrections for the readings obtained in the measurements of said physical variables, the prior art uses a temperature sensor in addition to the sensor for the particular variable being measured.

The co-pending application Ser. No. 10/251,416 describes a system for measuring oxygen pressure and temperature essentially simultaneously using a single oxygen-sensing photoluminescent probe, for example a ruthenium complex or a platinumn porphyrin, and an improvement on a previously patented system referred to as the Thermally Activated Direct Absorption (TADA) system, whereby the probe provides an indication of temperature without interference from and independent of the oxygen pressure acting on it. The reason there is no interference can be understood by noting that the measurement of the oxygen pressure is based on the oxygen quenching of the photoluminescence of the probe material (that is, a decrease of the luminescence quantum efficiency), a processes which occurs after the absorption of the luminescence excitation light, whereas the physical process indicative of the probe temperature is a temperature-dependent light absorption process which occurs prior to the photoluminescence and is not, therefore, affected by any processes which affect the photoluminescence efficiency, provided that the photoluminescence intensity is measurable to the needed extent. This is an easily met requirement given the great sensitivity of light detectors for visible and near infrared radiation. Once the temperature has been determined, a known temperature correction factor can be applied to the oxygen pressure reading provided by the same probe. The instrument used for measuring temperature and oxygen pressure is therefore substantially simplified compared to the prior art using two probes.

The situation is fundamentally more complex when one wishes to measure temperature with the same photoluminescent probe used for measuring a physical variable which, unlike oxygen pressure, modifies the optical absorption and/or luminescence bands of the probe material. Such physical variables include strong electric and magnetic fields. The effects of these fields are manifested by spectral shifts of the position and/or polarization of relatively narrow electronic absorption bands in rare earth-doped crystals, glasses or semiconductors. Magnetic fields affect the polarized absorption properties of rare earth ions like trivalent terbium, a phenomenon referred to as the optical Faraday effect, or the position of the peak absorption wavelength of one or more narrow absorption and/or photoluminescence bands (Zeeman effect). The peak wavelengths of said band can also be shifted by strong electric fields (Stark effect). Other electric field effects, for example the Franz-Keldysh effect, cause a spectral shift of the absorption band of semiconductors. But such shift is also temperature-dependent, and this cross sensitivity has made unreliable the optical measurement of electric fields using the Franz-Keldysh effect.

The co-pending application Ser. No. 10/251,416 disclosed, inter alia, a method for measuring temperature which is not affected by the oxygen quenching of the photoluminescence of the probe material. The method involves the use two different luminescence excitation wavelengths for exciting the probe material to the same electronic level, and the measurement of the relative intensities of the luminescence generated by the two wavelengths. A fraction $\alpha_1$ of the excitation light of wavelength $\lambda_1$ and power $P_1$ is absorbed by the probe to generate a luminescence light emitted with an intensity $I_1$, and a fraction $\alpha_T$ of the excitation light of wavelength $\lambda$, and power $P_T$ is absorbed by the probe to generate a luminescence light emitted with an intensity $I_T$. The two excitation wavelengths are chosen so that $\alpha_T$ and, therefore, $I_T$, have a much stronger temperature dependence than $\alpha_1$ and $I_1$. The temperature is then a unique function of the ratio $(I_T P_1 / I_1 P_T)$.

It turns out, as shown below, that ratio $(I_T P_1 / I_1 P_T)$ is also a reliable temperature indicator even if the photoluminescent probe is under a physical field that generates a measurable broadening or shift of the position of the peak absorption wavelength of one or more absorption and/or photoluminescence bands of the probe material. Therefore, the instant invention makes it practical to use a single photoluminescent probe to measure not only temperature and oxygen pressure, but also temperature and other physical variables, including some variables which affect the spectral properties of the probe material, like electric or magnetic fields.

OBJECTIVES OF THE INVENTION

It is the main object of the present invention to provide simple and inexpensive optical methods and instrumentation for measuring the temperature of objects or environments in the presence of other, simultaneously acting physical or chemical variables.

It is another object of the present invention to improve the TADA system so it can be used in temperature ranges within which the luminescence efficiency of the probe is substantially degraded.

It is yet another object of the present invention to improve the TADA system so it can be used with optical probe materials the electronic energy levels of which are shifted under the influence of another physical parameter.

It is another object of the invention to provide improved systems for the optical measurement of diverse physical parameters while providing temperature compensation, using a single probe.

It is one specific object of the present invention to provide simple and inexpensive methods and instrumentation whereby a single probe is used to measure both an electric field and temperature essentially at the same time and independently of each other.

It is another specific object of the present invention to provide simple and inexpensive methods and instrumentation whereby a single probe is used to measure both a magnetic field and temperature essentially at the same time and independently of each other.

Definitions

Within the context of this application, I am using the following definitions:

Light: optical radiation, whether or not visible to the human eye.

$cm^{-1}$: energy units expressed as the inverse of the corresponding wavelength $\lambda$ when the wavelength is given in centimeters (cm).

Excitation light: illuminating light which can generate luminescence in a luminescent material.

Interrogating light: illuminating light injected into or incident on an optical probe for the physical variable.

Luminescence: Light emitted by a material upon absorption of light or other radiation of sufficient quantum energy. The term includes both fluorescence and phosphorescence.

Luminescence centers: atoms or molecules (including ions) of a photoluminescent material which absorb excitation light and emit luminescence light.

Luminescence decay time T: the time after the cessation of the excitation radiation in which the intensity of the luminescence decays from $I_o$ to $I_o/e$, where e is equal to 2.71828 and $I_o$ is the luminescence intensity at any reference time chosen as "zero" time.

Luminescence quantum efficiency $\Phi$ (also referred to as luminescence efficiency): the ratio of the number of luminescence photons emitted by a luminescent material to the number of photons of the excitation light absorbed by the material.

Luminescence time rate of decay: the inverse of luminescence decay time T.

Single Luminophor: a photoluminescent material, whether pure, dissolved or dispersed in a polymer matrix, a glass or a paint, having a single light-emitting species, for example a specific platinum(I) porphyrin, or a specific ruthenium(II) complex with tris(4,7-diphenyl-1,10-phenanthroline), but not a composition containing both. Other example: $Nd^{3+}$ or other specific rare earth ion whether as a dopant or in a stoichiometric compound.

Occupancy number of an energy level: the fraction of the total number of molecules of a probe material occupying said energy level.

Paint: a relatively thin coating, whether or not colored, applied to an object as a sensing probe.

Photoluminescence: Luminescence generated by the absorption of light.

Physical variable: any physical (including chemical) property whose magnitude can change. Examples: pressure, temperature, flow rate, position, liquid level, oxygen and the like. (Synonims: measurand, physical parameter).

$\lambda_1$: wavelength of luminescence excitation light the optical absorption of which is not substantially affected by temperature.

$\lambda_v$: wavelength of luminescence excitation light the optical absorption of which is substantially temperature-dependent.

BRIEF SUMMARY OF THE INVENTION

The present invention improves and substantially extends the scope of the temperature measurement system based on the direct measurement of a temperature-dependent optical absorption by photoluminescent probes. That system, as described in section 2.1 of U.S. Pat. No. 5,499,313, and referred to herein as the Thermally Activated Direct Absorption (TADA) system, is based on a physical property shared by virtually all liquid or solid materials having an optical electronic absorption band in the visible or near infrared region of the optical spectrum. When these materials are illuminated with light of any wavelength or wavelengths $\lambda_v$, within the long wavelength tail of their lowest energy electronic absorption band, the magnitude of the fraction $\alpha$ of the intensity of the light which is absorbed is temperature-dependent, increasing in a known manner with increasing temperature. If these materials are photoluminescent, the luminescence intensity generated by the absorption of light of said wavelength or wavelengths $\lambda_v$ is also temperature-dependent, this intensity increasing in a manner directly proportional to the magnitude of $\alpha$ if the luminescence quantum efficiency of the photoluminescent material is not degraded over the temperature range of operation. A measurement of a luminescence intensity directly proportional to $\alpha$ is a direct measurement of light absorption, in contract to light transmission measurements, where the value of $\alpha$ is determined indirectly as a difference between two light intensities, not measured directly. U.S. Pat. No. 5,499,313 teaches how to measure temperature at any chosen point with a discrete sensor of known composition and thickness, and how to extend its main concept to the measurement of distributed temperatures by using a suitably doped long optical fiber probe.

The instant invention improves and substantially extends the TADA system so it can be used in temperature ranges within which the luminescence efficiency of the probe is substantially degraded.

Furthermore, the instant invention teaches new techniques for further extending the reach of the TADA system to allow a single photoluminescent probe material to be used for both temperature and oxygen and air pressure measurements, essentially simultaneously and independently of each other, whether the measurement is done on a discrete point, or averaged over a finite surface, or over each of a plurality of points distributed over a surface.

The technology subject of this invention can also be used for measuring temperature with any probe used for sensing concurrently any other physical or chemical measurand, provided the probe uses an efficient photoluminescent indicator, whether the indicator is unchanged, generated or partially consumed in the process.

The instant invention extends the capability of these techniques still further, by allowing the measurement of air pressure and temperature distributions over the surface of a body subject to these air pressure and temperature distributions. The invention permits these measurements with reasonably high accuracy using as sensors photoluminescent coatings even when the sensing points on the coatings are of non-uniform thickness and would, under the prior art techniques, generate many erroneous readings due to their different light absorption path lengths. The invention includes features for cancelling out the effects of these different thicknesses by performing measurements in two different wavelength regions and comparing the readings obtained from these two wavelength regions.

Still further, the instant invention makes it possible to measure accurately the surface temperatures of fast moving bodies, for example rotating turbine blades. In the prior art these measurements use as probes paints applied to the surface of said bodies, the paints including a thermographic phosphor, that is a photolumin scent material having a temperature-dependent luminescence decay time $T_T$. The measurements are carried out by exciting the luminescence of the paint with pulses of light of microsecond or sub-microsecond duration and measuring the luminescence decay time $T_T$. A serious disadvantage of this method is that, in a fast moving body one has to measure the intensities of two short duration fractions of the time-decaying luminescence from the illuminated spot. The first fraction is measured very shortly after the extinction of the excitation pulse, before the peak luminescence intensity has decayed significantly. The second fraction is measured a short interval afterwards, as the spot has moved rapidly away from the position where the intensity of its first luminescence portion was measured. Now, except for a relatively small group of materials described in Kleinerman's U.S. Pat. No. 5,222,810 section 2.0: Luminescent Materials Having two Emissive Levels with Temperature-Dependent Relative Populations, a decrease in the luminescence decay time T of a probe with increasing temperature parallels a decrease in its luminescence efficiency, which inevitably decreases the signal-to-noise ratio of the measurement. In the high temperature region (above 500° C.) within which the luminescence decay time T decreases appreciably per increasing degree the luminescence quantum efficiencies are often of the order of $10^{-2}$ or smaller. And since only a small fraction of the emitted luminescence intensity is measured, the measurement accuracy is limited. Another source of error has recently been pointed out by J. P. Feist et al. (*Measurement Science and Technology* 14 N17–N20 (2003)): the temperature readings are affected by oxygen quenching, which decreases the luminescence decay time $T_T$ further from the value of $T_T$ caused by temperature alone.

Yet further, the instant invention allows the measurement, with a single photoluminescent probe, of temperature and other physical variables, for example electric currents, electric fields or magnetic fields, even when said fields modify the electronic absorption and/or luminescence spectra of the probe material.

Perhaps a more serious disadvantage of thermographic phosphors based on a temperature-dependent luminescence decay time (other than the relatively small group comprised of materials having two emissive levels with temperature-dependent relative populations) is that they have a relatively narrow temperature range of usefulness. They are not useful at temperatures below which there is no appreciable luminescence quenching.

The present invention overcomes these shortcomings and permits the measurement of temperatures and surface temperature distributions independently of oxygen pressure, with photoluminescent probes which maintain their high luminescence efficiencies over their temperature range of operation and do not require a temperature-dependent change in their luminescence spectral distribution, luminescence efficiency or decay time. Any contribution of oxygen pressure to the decay time can then be determined by comparing the value of $T_T$ to that determined by temperature alone.

PHYSICAL BASIS OF RELATED PRIOR ART

1. Thermally-activated Optical Absorption Processes in Photoluminescent and Other Materials The technology to be described uses the fact that all solid and liquid materials which absorb light of visible or near infrared wavelengths have a temperature-dependent optical absorption at the long wavelength tail of an electronic absorption band. If the materials are photoluminescent and absorb only a small fraction of the intensity of the incident light, the intensity of the photoluminescence is the most convenient indicator of the magnitude of the optical absorption. This can be understood with the help of FIG. 1. The analysis that follows, taken from Kleinerman's U.S. Pat. No. 5,499,313, is deliberately oversimplified to emphasize the aspects most relevant to the invention. The quantitative relationships may not be followed rigorously in all practical systems. I do not wish to be bound by theory, and the account that follows must be taken as a model for understanding how the absorption of light of some wavelengths by a material, and the luminescence intensity generated by the absorbed light, can increase substantially and predictably with increasing temperature.

Figure 1:
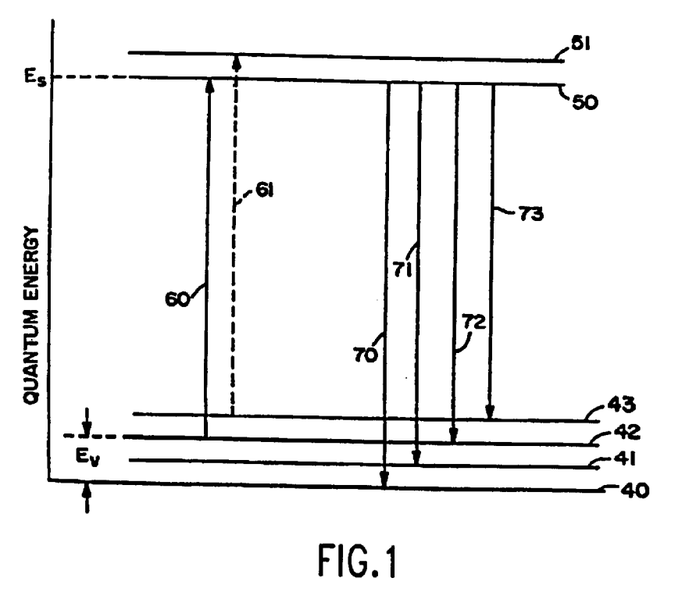
FIG. 1 is a simplified molecular energy diagram illustrating a temperature-dependent optical absorption process and luminescence conversion of the absorbed light in most photoluminescent materials.

FIG. 1 shows a diagram of electronic energy levels and transitions which at least qualitatively describes, at the molecular level, most luminescent materials. The luminescent material includes, at the atomic or molecular level, luminescence centers having a ground electronic level comprising vibrational sublevels 40, 41, 42, 43 and other sublevels which, for the sake of simplicity, are not shown.

The lowest excited electronic energy level comprises sublevels 50, 51, and any other sublevels not shown. The vertical arrowed line 60 represents an optical electronic transition produced by the absorbed excitation light from sub-level 42 to excited level 50, which have fixed energy levels $E_v$ and $E_s$, respectively, relative to the ground level 40 (The subscript "v" originated from the fact that in most photoluminescent materials the thermally excited sub-level is "vibronic"). The length of line 60 corresponds to the photon energy of the optical transition and, hence, to the specific wavelength $\lambda_v$ of the excitation light. This wavelength, usually in the long wavelength 'tail' of the electronic absorption band, obeys the relation:

$$\lambda_v = hc/(E_s - E_v) \text{ centimeters(cm)} \qquad (1)$$

where h is Planck's constant and c is the velocity of light in free space. The wavelength $\lambda_v$ can excite only molecules occupying vibrational level 2 and, to a smaller extent, molecules occupying slightly higher levels, the excitation of which is represented by the dotted vertical line 61. Luminescence emission occurs from level 50 to the different sublevels of the ground electronic level, said emission represented by lines 70, 71, 72 and 73. As shown in FIG. 1, a considerable spectral portion of the emission occurs at photon energies higher (and wavelengths shorter) than that of the excitation light, and is commonly referred to as anti-Stokes emission.

In practice the photoluminescent material used in a temperature probe is usually a solid solution, glassy or crystalline, which constitutes the probe. The concentration of the photoluminescent material and the dimension of the probe along the direction of the interrogating light are chosen so that the probe absorbs only a temperature-dependent fraction $\alpha_T$ of the intensity of the nearly monochromatic excitation light within the temperature range of operation, and transmits the rest. At relatively low optical densities the fraction $\alpha_T$ of the intensity P of the interrogating light absorbed by the molecules occupying the sublevel 3 obeys the relation:

$$\alpha_T = K N_{42}/N_{40} \tag{2}$$

where $N_{42}$ is the number of molecules of the photoluminescent material occupying vibrational level 42;

$N_{40}$ is the number of the molecules of the photoluminescent material occupying level 42; and K is a constant specific to the probe
Now $$N_{42}/N = \exp(-E_v/kT) \tag{3}$$

At optical densities no greater than about 0.02 $\alpha$ is given approximately by:

$$\alpha_T = K \cdot \exp(-E_v/kT) \tag{4}$$

where k is the Boltzmann factor and T the absolute temperature in kelvins. At optical densities greater than 0.02 the relationship between $\alpha$ and the Boltzmann factor $\exp(-E_v/kT)$ becomes less linear, but equations (2) and (3) still hold, and the method can be used at high, low or intermediate optical densities.

The luminescence intensity $I_T$ generated by the interrogating light absorbed by the probe obeys the relation:

$$I_T = P_T \cdot \phi K \cdot \exp(-E_v/kT) \text{ photons.sec}^{-1} \tag{5}$$

where $P_T$ is the intensity of the incident interrogating light in photons.sec$^{-1}$, and $\phi$ is the luminescence quantum efficiency of the photoluminescent material.

Probes made from materials having high $\phi$ values can produce large signal-to-noise ratios even with optical densities lower than 0.01, provided that the optical system has at least a moderately high collection efficiency for the probe luminescence. Such efficiency is easily obtainable with state-of-the-art systems.

The temperature coefficient of the luminescence intensity follows approximately the relation:

$$(1/I_{T0})(dI_T/dT) = E_v/kT^2 = \beta/T^2 \text{ deg}^{-1} \tag{6}$$

where $I_{T0}$ is the luminescence intensity at a chosen reference temperature. For example, a material with an energy $E_v$ of 1200 cm$^{-1}$ has a coefficient of about two percent per kelvin at an ambient temperature of 295 K. Equation (6) assumes that the luminescence quantum efficiency $\phi$ is substantially independent of temperature over the temperature range of application of the method. Note that for any value of $(E_v/kT)$ the temperature coefficient of the luminescence intensity $I_f$ increases as the initial absolute temperature decreases, and it is orders of magnitude greater in the cryogenic liquid helium range (less than 4.2 kelvins) than at ordinary temperatures.

Equations (4) to (6) show that the method of the preceding paragraphs requires only a temperature-dependent change in the optical absorption coefficient of the luminescent probe material at wavelengths corresponding to photon energies lower than the energy $E_s$ of the excited emissive level. This property is shared by virtually all luminescent materials. The method does not require any temperature-dependent changes in the luminescence quantum efficiency, spectral distribution or decay time T. Therefore, it can be implemented with most luminescent materials. Practical considerations favor a value of $E_v$ between 3 kT and 7 kT.

Figure 2:
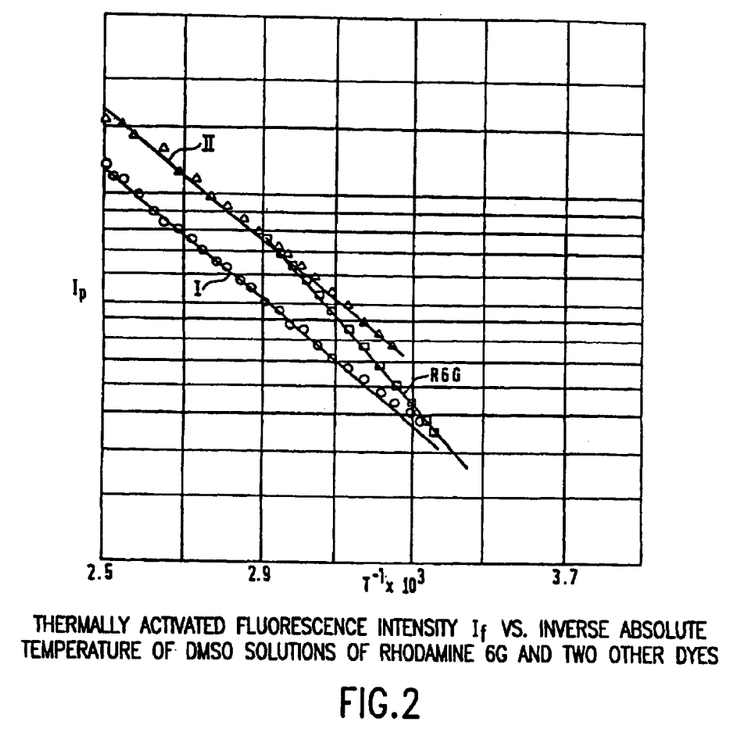
FIG. 2 shows the temperature dependence of the normalized thermally activated fluorescence intensities of three organic dyes as a function of the inverse absolute temperature.

Experimental tests of equations (4) to (6) have been carried out with liquid solutions of three different dyes dissolved in dimethyl sulfoxide (DMSO). Two of the dyes, dye I and dye II are represented by the chemical structures:

Dye I is the sulfonated derivative of Hostasol Red GG (American Hoechst Corp.). Dye II has been described in U.S. Pat. No. 4,005,111 by Mach et. al. The third dye was the well known Rhodamine 6G (R6G). The dyes were dissolved in DMSO at concentrations of the order of $10^{-4}$ Molar and excited with light from a He-Ne laser ($\lambda_v = 633$ nm) in a square cuvette. The fluorescence intensity was monitored at the wavelength of 612 nm, shorter than the wavelength of the excitation light. The experimentally measured fluorescence intensities $I_f$ were measured as a function of the absolute temperature T. Plots of $I_T$ v. $T^{-1}$ are shown in FIG. 2 for the three dyes. The behavior predicted by equations (3) and (5) was confirmed. The slopes of the lines drawn through the experimental points give $E_v$ values of 1380, 1355 and 1890 cm$^{-1}$ for dyes I, II and R6G, respectively. When these values are added to the excitation photon energy of 15803 cm$^{-1}$, one obtains $E_s$ values of $1.72 \times 10^4$ cm$^{-1}$ for dyes I and II, and $1.77 \times 10^4$ cm$^{-1}$ for R6G. These values are in good agreement with the $E_s$ values determined from the fluorescence spectra of these dyes.

Figure 3:
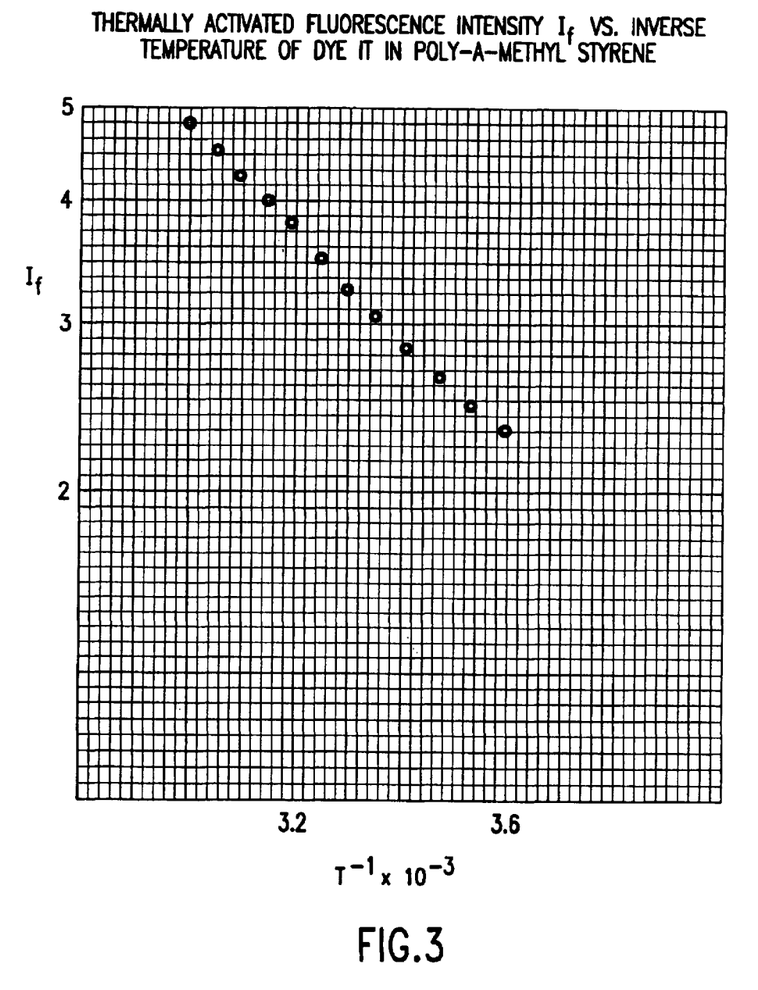
FIG. 3 shows the temperature dependence of the normalized thermally activated fluorescence intensity of a polymer solution of an organic dye as a function of the inverse absolute temperature.

Dye II was incorporated into a poly-α-methyl styrene plastic at a concentration of the order of 0.01 Molar. FIG. 3 shows the temperature dependence of its normalized fluorescence intensity $I_f$ over a temperature range of medical interest.

DETAILED DESCRIPTION OF THE INVENTION

2. Elimination of Luminescence Efficiency Effects in TADA Temperature Measurements The TADA method as described above is applicable for systems that use photoluminescent materials having an essentially constant luminesc nce quantum efficiency φ over the temperature range of application of the method. It is to be noted that derivation of equation (6) from equation (5) assumes that constancy. It is one of the main features of the instant invention that it xtends the applicability of the TADA method to temperature ranges wherein the value of φ varies substantially, usually decreasing with increasing temperature.

The improved TADA method is based on the fact that, while the absorbed fraction $\alpha_T$ of the intensity of light of wavelength or wavelengths $\lambda_v$ in the long wavelength 'tail' of the electronic absorption band of the probe material increases substantially with increasing temperature, and generates a luminescence of intensity $I_T$, if the same material is excited with light of shorter wavelength or wavelengths $\lambda_1$, for example near the peak of the same electronic absorption band, the absorbed fraction $\alpha_1$ of the light intensity has relatively little or no temperature dependence, or may even decrease with increasing temperature, and generates a luminescence of intensity $I_1$ directly proportional to $\alpha_1$. The ratio $I_T/I_1$ of these intensities is an unambiguous temperature indicator independent of the value of φ, even if this value is temperature-dependent. This follows from the following analysis:

The luminescence intensity $I_1$ in photons.sec$^{-1}$ follows the relation:

$$I_1 = P_1 \alpha_1 \phi \quad (7)$$

The absorbed fraction $\alpha_T$ of the light of wavelength $\lambda_v$ follows equation (4), that is, $\alpha_T = K.\exp(-E_v/kT)$. Therefore the luminescence intensity $I_T$ measured by a suitable photodetector (which can be either the same one used for measuring $I_1$ or a second photodetector) follows the relation:

$$I_T = P_T K \phi \exp(-E_v/kT) \quad (8)$$

Since both excitation wavelengths are within the same absorption band the luminescence quantum efficiency φ is the same. Dividing $I_T$ by $I_1$ we get:

$$(I_T P_1 / I_1 P_T) = (K/\alpha_1) \exp(-E_v/kT) \quad (60)$$

Now, writing A for $(K/\alpha_1)$ and solving for T one gets the relation:

$$T = A \cdot E_v \cdot k / \ln(I_T P_1 / I_1 P_T) \text{ kelvins} \quad (9)$$

where A is a constant, ln is shorthand for naperian logarithm, and φ has been canceled out! This means, inter alia, that the system can still be used at temperatures much higher than that at which the quantum efficiency φ starts decreasing.

Whether or not equations (4)–(6) or (8) are rigorously obeyed by an actual system, the ratio $(I_T P_1/I_1 P_T)$ is a reproducible and accurate temperature indicator, regardless of the oxygen pressure or any parameter that affects the quantum efficiency, spectral distribution or decay time T of the generated luminescence.

3. Measurement of Temperature and Oxygen Pressure with a Single Probe

The main feature of this invention is the ability to measure temperature and oxygen pressure, each independently of the measurement of the other, simultaneously or quasi-simultaneously (within one or a few seconds) using a single photoluminescent material as a probe for both parameters. The measurements can be independent of each other because oxygen pressure affects the luminescence quantum efficiency and decay time T of the probe after the luminescence excitation light has been absorbed, independently of the wavelength of the excitation light, whereas the temperature measurement depends on a temperature-dependent light absorption property at a pre-selected wavelength before any luminescence light is emitted, independently of anything that affects the luminescence emission.

Now, the oxygen pressure reading does depend on temperature in a manner that can easily be predetermined, but since the temperature readings can be made independent of the oxygen pressure, as shown below, any temperature effect on the oxygen pressure reading can be easily compensated to give a temperature-corrected reading.

For any specific oxygen photoluminescent probe based on the oxygen effect on the normalized luminescence intensity and/or decay time T one can determine, in a controlled experiment, the effect of varying oxygen pressure on the normalized luminescence intensity or the decay time T of the probe at a given temperature. Then, for any known oxygen pressure one can vary the temperature in a controlled manner to obtain the temperature effect on the measured luminescence intensity or the decay time T, referenced to any chosen temperature. Once such data have been obtained and stored in memory, any oxygen pressure reading at any measured temperature can be temperature-corrected to obtain the true value of the oxygen pressure.

Equations (4) to (6) are at least approximately valid for all photoluminescent materials, so they apply to the ruthenium complexes and the platinum porphyrins mentioned above, which are popular oxygen sensing dyes.

3.1 Measurement of Spot Temperature and Oxygen Pressure

Spot measurements of oxygen pressure and temperature can be conveniently carried out with the oxygen sensor, for example a platinum porphyrin, immobilized in an oxygen-permeable matrix attached to the tip of an optical fiber. Before the measurements are carried out, the probe is calibrated as follows:

(a) A fluorescence spectral response curve is constructed for the probe and the optical system used, namely a plot of its fluorescence intensity $I_\lambda$ as a function of excitation wavelength at a reference temperature, normalized to a constant intensity for the excitation light and for optical densities substantially lower than 1.0, for a spectral region from just past the peak of its longest wavelength electronic absorption band to longer wavelengths within the tail of the band which can be absorbed only by molecules occupying a thermally excited level. Within this spectral region, two excitation light sources of narrow wavelength bands $\lambda_1$ and $\lambda_v$, respectively, are chosen so that the absorption of light of wavelengths $\lambda_1$ and intensity $P_1$ is independent or only minimally dependent on temperature and generates a relatively strong luminescence intensity $I_1$ with relatively little or no temperature dependence, and the light of wavelengths $\lambda_v$ and intensity $P_T$ is absorbed only by molecules occupying a thermally excited level of energy $E_v$ above the ground level, thus generating a luminescence intensity $I_T$ which has a strong temperature dependence consistent with a convenient signal-to-noise ratio. (The most suitable wavelengths $\lambda_1$ are usually at or near the peak of the lowest energy electronic absorption band. The wavelengths $\lambda_v$ are usually at or near the bottom of the long wavelength 'tail' of the same band).

(b) For each of the excitation lights of wavelengths $\lambda_1$ and $\lambda_v$ of intensities $P_1$ and $P_T$, respectively, construct a luminescence intensity $I_T$ vs. absolute temperature T plot for the temperature range of operation, other things being equal.

(c) For a constant (or normalized) intensity $P_1$ of the excitation light of wavelength $\lambda_1$, and at each temperature within a multiplicity of temperatures within the temperature range of operation, construct a plot of the luminescence decay time T or the normalized luminescence intensity vs. oxygen pressure over the range of oxygen pressures to be measured. An oxygen-dependent normalized luminescence intensity can be obtain d, for example, by comparing the luminescence intensity of the oxygen-sensitive dye to the intensity of the excitation light reflected by the probe. These plots are especially important if T (or the normalized luminescence intensity) decreases in a known manner with increasing temperature as the luminescence quantum efficiency of the paint decreases.

Once the probe has been calibrated, the temperature being measured can be determined unambiguously from the ratio $(I_T P_1 / I_1 P_T)$ as shown in section 2. The oxygen pressure can be determined from T. The measurement of a luminescence decay time is straightforward and well known to workers in the art having at last average competence. To the extent that T or the normalized luminescence intensity may depend on temperature, the temperature obtained from the ratio $(I_T P_1 / I_1 P_T)$ can be effectively used for providing a temperature compensation factor for the measured T values.

Photoluminescent Materials Suitable for the Practice of this Invention

The technology subject of this invention for sensing both oxygen pressure and temperature with a single probe can be used with any photoluminescent material the luminescence of which is partially quenched by oxygen. Therefore, all photoluminescent materials used in the prior art as oxygen probes are suitable. The most widely used materials are ruthenium(II) complexes with tris(4,7-diphenyl-1,10-phenanthroline) and platinum porphyrins. Their current use is due perhaps more to technological inertia than to their instrumental suitability. They require excitation light sources in the green and yellow spectral regions, for which small inexpensive diode lasers are not yet available (although suitable LEDs are available). Small, efficient, inexpensive diode lasers are available in the red region for wavelengths from about 630 to about 690 nanometers (nm) and in the near infrared region. It should be advantageous to use oxyquenchable photoluminescent materials having absorption bands in these regions, especially for applications where the luminescence signals generated by LED excitation may be too weak to provide an adequate signal-to-noise ratio. An example of a suitable material is the dye platinum (I) tetraphenyl tetrabenzoporphyrin, described in U.S. Pat. No. 6,207,461 to Baumann, which can be excited in the red region. Laser diodes have an added advantage over LEDs in than they generate light having much narrower bands, and narrow bands are desired for light of wavelengths $\lambda_v$, in order to better define the value of the energy $E_v$.

3.2 Alternate Method and Device for the Measurement of Temperature and Oxygen Pressure with a Single Probe Instead of measuring both oxygen pressure and temperature with the same oxygen sensing material as as described in the previous section one may incorporate a second photoluminescent material for measuring temperature, according to the TADA method, within the optical fiber itself near the tip in contact with the oxygen sensing material. Preferably said second material should have optical absorption and luminescence bands different from those of the pressure sensing material. An example of a suitable temperature sensing material is a glass doped with trivalent ytterbium ($Yb^{3+}$). It has a relatively narrow luminescence band at wavelengths near 975 nm, and it can be excited with a relatively inexpensive microlaser at the Nd:YAG laser wavelength of 1.06 micrometers ($\mu$m), in this case the wavelength $\lambda_v$. At this excitation wavelength the value of $E_v$ for $Yb^{3+}$ is approximately 860 $cm^{-1}$. These are widely separated from the excitation and luminescence wavelengths of most oxygen sensing materials. The $Yb^{3+}$-doped glass can be a short silica glass fiber segment fused or otherwise attached to a glass optical fiber guide used for transmitting the excitation lights to the probe.

In a suitable arrangement, the dye platinum(I) tetraphenyl tetrabenzoporphyrin is immobilized within an oxygen-permeable matrix attached to the tip of an $Yb^{3+}$-doped glass fiber segment fused to a glass optical fiber.

4. Surface Temperature Measurements on Moving Objects

The instant invention makes it possible to measure the surface temperatures of fast moving bodies, for example rotating turbine blades, using as probes efficient phosphors, whether or not they have temperature-dependent luminescence decay times or substantially temperature-dependent luminescence spectral distributions. In the prior art these measurements used as probes paints applied to the surface of said bodies, the paints including a photoluminescent material having a substantially temperature-dependent luminescence decay time T. The measurements are carried out by exciting the luminescence of the paint with pulses of light of sub-microsecond duration and measuring the luminescence decay. A serious disadvantage of this method is that, in a fast moving body one has to measure the intensities of two short duration fractions of the time-decaying luminescence from the illuminated spot. The first fraction is measured very shortly after the extinction of the excitation pulse, before the peak luminescence intensity has decayed significantly. The second fraction is measured a short interval afterwards, as the spot has moved rapidly away from the position where the intensity of its first luminescence portion was measured. Now, except for a relatively small group of materials described in Kleinerman's U.S. Pat. No. 5,222,810 section 2.0: Luminescent Materials Having two Emissive Levels with Temperature-Dependent Relative Populations, a decrease in the luminescence decay time T of a probe with increasing temperature parallels a decrease in its luminescence efficiency, which inevitably decreases the signal-to-noise ratio of the measurement. In the high temperature region (above 500° C.) within which the luminescence decay time T decreases appreciably per increasing degree the luminescence quantum efficiencies are often of the order of $10^{-2}$ or smaller. And since only a small fraction of the emitted luminescence intensity is measured, measurement accuracy is limited.

The present invention overcomes these shortcomings and permits the measurement of temperatures and surface temperature distributions with photoluminescent probes which maintain their high luminescence efficiencies over their temperature range of operation and do not require a temperature-dependent change in their luminescence spectral distribution or luminescence efficiency.

For example, $Dy^{3+}$-doped $LuPO_4$ has a luminescence decay time T of about 700 microseconds ($\mu$sec) which is essentially constant from ordinary temperatures up to about 1,200K, so it cannot be used as a temperature probe in the decay time mode. Nd:YAG has a luminescence decay time which changes only slowly with increasing temperature over a substantial temperature range. With these photoluminescent materials, the TADA method and its associated instrumentation provides better temperature measuring capabilities, especially within the temperature ranges within which their luminescence decay times do not vary substantially. For example, $Dy^{3+}$ has an electronic energy level $^6H_{13/2}$ about 3,300 cm$^{-1}$ above the $^6H_{15/2}$ ground level, which can be significantly excited thermally at temperatures from about 800K and higher. Light of wavelength $\lambda_v$ of 570 nm excites the $Dy^{3+}$ ions occupying that level to the excited emissive level $^4F_{9/2}$, generating a luminescence intensity with a temperature coefficient greater than 0.5 percent per kelvin below 1,200K. $Nd^{3+}$ ions occupying the thermally excited level $^4I_{11/12}$ can be optically excited, in $Nd^{3+}$-doped phosphors, with light of 1.064 micrometers ($\mu$m) wavelength $\lambda_v$ to the $^4F_{3/2}$ emissive level, or with a $\lambda_v$ of 660 nm to the $^4G_{5/2}$ level. $Eu^{3+}$ ions occupying the thermally excited levels $^7F_2$, $^7F_3$, and $^7F_4$ can be optically excited, in $Eu^{3+}$-doped phosphors, to the emissive level $^5D_0$ with lights of wavelengths of about 612, 650 and 701 nm, respectively, or the $^5D_1$ level with lights of wavelengths of 553, 583 and 626 nm, respectively.

The procedure and associated instrumentation follow essentially the teachings of section 3.1 above for measuring temperature using two excitation lights of wavelengths $\lambda_1$ and $\lambda_v$ as defined therein.

Within the temperature region where the luminescence decay time decreases substantially with an increase in temperature, the TADA method as used according to the invention provides a means for verifying the temperature readings thus obtained with the temperature-dependent luminescence decay time method.

Preferred Embodiments

The preferred embodiments according to the instant invention depend on the desired temperature range of operation. For measuring the temperature of rotating turbine blades, for example, the outer surface of a blade (facing the observer) is coated with a paint containing a phosphor which retains, at the upper end of the working temperature range, no less than about one tenth of its luminescence efficiency at ordinary temperatures. Now, suppose that the turbine rotor is spinning at 15,000 RPM, that is 250 revolutions per second, and that the diameter of the rotor including the blades is 1 meter. The linear velocity of the rotating blade is then 7.85×10$^4$ cm/sec. Assume also that a 1 cm$^2$ area of the coated surface near the outer radial edge of the blade is within the fields of view of two excitation light sources and the photodetector. That strip will be under the excitation light for about 12.7 microseconds ($\mu$sec) per revolution. One of the two excitation light sources illuminates said area with light of wavelength $\lambda_1$ as defined above, that is light the absorption of which by the paint has a small or zero temperature dependence, as defined in sections 2 and 3.1 above. This light, of intensity $P_1$, generates a luminescence of intensity $I_1$. The other excitation light source illuminates the same area with light of wavelength $\lambda_v$, the absorption of which is strongly temperature-dependent as defined above. This light has an intensity $P_2$ and generates a luminescence of intensity $I_T$. The paint is illuminated alternately by the two light sources, one for each revolution of the rotor. For each of the two lights, there will be then 125 exposures per second of about 12.7 $\mu$sec_each. The photodetector signals from each of the the luminescence intensities thus generated are integrated for about one second. The temperature of the coated surface is determined from equation (9) above. If the temperature range of operation is from about 600K to about 1000K a suitable phosphor is $Nd^{3+}$-doped yttrium aluminum garnet (Nd:YAG). The wavelength $\lambda_1$ is about 880 nm and excites molecules occupying the ground level $^4I_{9/12}$ to the $^4F_{3/2}$ emissive level. $\lambda_v$ is about 1.064 $\mu$m and excites molecules occupying the thermally excited level $^4I_{11/12}$ to the same $^4F_{3/2}$ emissive level. One of the attractive features of the Nd:YAG phosphor is that both excitation wavelengths are generated by commercially available and relatively inexpensive lasers.

5.0 The Measurement of Surface Temperature Distributions

The prior art for measuring surface temperature distributions uses a temperature sensing paint containing a photoluminescent material applied to the surface on which the temperature distribution is to be measured, and photographic or photo-electronic video imaging techniques. Usually the photoluminescent material has a temperature-dependent luminescence decay time T. The paint is illuminated with a pulse of luminescence excitation light of much shorter duration than T. Two successive short time 'slices' of the temperature-dependent luminescence spectral distribution are imaged on and processed by a CCD array or similar photo-electronic imaging device after the excitation light pulse is extinguished, both preferably before the time T. The relative luminescence intensities from each point at said two time 'slices' give the value of T and, hence, the temperature at each point on the illuminated paint.

In an alternate method one uses a paint including a luminophor having a temperature-dependent luminescence spectral distribution, not necessarily a temperature-dependent luminescence decay time. The paint is illuminated with a CW or pulsed source of luminescence excitation light and the luminescence intensity distribution is focused as an image, through an optical filter that passes only a pre-selected set of wavelengths, on a CCD array or similar digital photo-electronic imaging device. The same luminescence intensity distribution is focused as an image, through another optical filter that passes only a different pre-selected set of wavelengths, on a second photo-electronic imaging device. The relative intensities of the two sets of wavelengths from each point on the coated surface indicate the temperature at that point.

Both of the above methods have disadvantages. A method based on a temperature-dependent luminescence decay time T is quite adequate, even preferable to other methods for measuring temperatures at a discrete point, mainly because a decay time can be converted into a frequency, and the measurement of a frequency is less prone to errors than the measurement of a luminescence intensity. But this advantage is lost when measuring surface temperature distributions with imaging video devices, wherein one must measure relatively low luminescence intensity distributions. And the method based on a temperature-dependent luminescence spectral distribution requires the measurement of relatively small spectral fractions of the luminescence emission of the luminophor, thus seriously diminishing the signal-to-noise ratio.

This invention uses a paint wherein the sensing entity is a photoluminescent material dissolved or dispersed therein. The measuring arrangement is substantially similar to the photo-electronic arrangement of the prior art that uses a paint with a photoluminescent material having a temperature-dependent luminescence decay time, except that neither the luminescence decay time, nor the luminescence quantum efficiency nor the luminescence spectral distribution of the photoluminescent material of this invention need be temperature-dependent, provided that the luminescence of said material can be excited by light of wavelength $\lambda_v$ the absorption of which is temperature-dependent as described above. A preferred embodiment uses a temperature sensing paint applied to the surface to be measured. The paint includes a photoluminescent material comprised of a single luminophor. The required area of the paint is illuminated successively by lights of wavelengths $\lambda_1$ and $\lambda_v$ (as defined above), respectively, thus generating luminescence images of distributed intensities $I_1$ and $I_T$, respectively. Two successive luminescence images of the coated surface, one excited by light of wavelength $\lambda_1$ and the second excited by light of wavelength $\lambda_v$, are focused and captured on a digital imaging device, preferably a video camera, digitized and processed by techniques well known in the prior art. The relative luminescence intensities from each and all resolvable smaller areas (pixels) within the illuminated area on the paint excited successively by lights of wavelengths $\lambda_1$ and $\lambda_v$ will be an accurate temperature indicator for said points, whether or not equations (4) to (6) are quantitatively accurate. To the extent that they are, the temperature of each point obeys equation (9) above, regardless of any thickness inhomogeneities in the paint. This can be understood from the following:

One starts from equation (7), where all the factors have been determined by the calibration steps (a) and (b) of section 3.1. We note that for any resolvable smaller area (point) on the luminescent paint, $I_1=P_1 \cdot \alpha_1 \cdot \phi$ Now, at low optical densities $\alpha_1$ is directly proportional to d, the thickness of the paint at that point. So, keeping in mind that $I_1$ is independent or only minimally temperature-dependent, we can write:

$$I_1 = K_1 \cdot P_1 \cdot d \cdot \phi$$

and $$I_T = K_2 \cdot P_T \cdot d \cdot \phi \cdot \exp(-E_v/kT)$$

where $K_1$ and $K_2$ are constants. So, dividing $I_T$ by $I_1$ and solving for T one gets equation (9) above, where both the thickness d at each point and the luminescence quantum yield $\phi$ (have been canceled out. Therefore, by using two pre-selected excitation wavelengths the temperature at each point over the paint is determined unambiguosly regardless of any thickness variations.

To summarize, successive illuminations of the paint with lights of wavelengths $\lambda_1$ and $\lambda_v$ generate luminescence distributions of intensities $I_1$ and $I_T$, respectively, at any and all said resolvable smaller areas (pixels), in such a manner that the ratio $(I_T \cdot P_1/I_1 P_T)$ for each of said points increases substantially in a known man with increasing temperature; substantially independent of any air pressure then acting on the paint or of any thickness inhomogeneities on it.

5.1. The Measurement of Temperature Distributions on the Surface of Moving Objects For measuring temperature distributions on the surface of moving objects one may use the same technique described in the preceding paragraphs, with the added proviso that the two successive luminescence images of the coated surface, one excited by light of wavelength $\lambda_1$ and the second excited by light of wavelength $\lambda_v$, are obtained while the moving surface is within the field of view of the light sources and the exposures are short enough that image is not blurred. The task is greatly simplified if the moving object is part of a fast revolving structure, like rotating turbine blades, because a large number of reproducible single exposures short enough to 'freeze' the motion can be integrated in order to increase the signal-to-noise ratio for each pixel.

6. An Alternate Method for Measuring Surface Temperature Distributions

Some photoluminescent materials have at least two excited missive levels having an energy difference $E_e$ such that, if the lower of these emissive levels has a relatively long decay time T (typically of the order of $10^{-4}$ seconds or longer) and is populated by optical excitation of molecules from the ground level, the molecules so excited distribute themselves between these two levels approximately as a function of the Boltzmann factor $\exp(-E_e/kT)$, where k is the Boltzmann constant and T is the absolute temperature in kelvins, as defined above. These two excited levels are referred to herein as being in a Boltzmann equilibrium. Examples of such systems were described in Kleinerman's U.S. Pat. No. 5,222,810 section 2.0: Luminescent Materials Having two Emissive Levels with Temperature-Dependent Relative Populations. If the rate of radiative decay from the higher excited level is not lower than that from the lower excited level, the luminescence intensity emitted from the higher level increases relative to that of the lower emissive level, and the spectral distribution of the total luminescence is changed. And if the probe is a paint, the relative intensities of the luminescence bands originating from the two emissive levels is an unambiguous temperature indicator, regardless of thickness variations at different sensing points.

One kind of photoluminescent materials having at least two excited emissive levels in a Boltzmann equilibrium are some $Cr^{3+}$-doped inorganic crystals wherein the excited emissive level $^4T_2$ level lies above the $^2E$ excited emissive level so that, upon absorption of light that excites either of these levels, there is a temperature range within which there is thermal excitation of molecules in the $^2E$ level to the $^4T_2$ level so that intensity of the luminescence spectral band originating at the $^4T_2$ level increases with increasing temperature at the expense of the intensity of the luminescence spectral band originating at the $^2E$ level.

Another kind of photoluminescent materials having at least two excited emissive levels in a Boltzmann equilibrium are some rare earth-doped inorganic crystals and glasses. For example, the trivalent neodymium ion $Nd^{3+}$ has a lower excited emissive level $^4F_{3/2}$ separated by an energy of about 1080 $cm^{-1}$ from the higher emissive level $^4F_{5/2}$. At temperatures above 800K (527° C.) the luminescence emission band at about 810 nanometers (nm) from the $^4F_{5/2}$ to the ground level $^4I_{9/2}$ becomes quite evident and its intensity increases relative to the luminescence intensity from the $^4F_{3/2}$ level. Temperature readings can be derived, then, from the temperature-dependent spectral distribution of the luminescence.

The invention subject of Kleinerman's U.S. Pat. No. 5,222,810 is limited to the measurement of spot temperatures. The instant invention is an improvement and extension of the concept of the Boltzmann equilibrium between two excited luminescent levels to the measurement of surface temperature distributions. Furthermore, it provides a means for verifying the temperature readings thus obtained with the independent luminescence intensities obtained from the TADA readings. If the photoluminescent material in a temperature sensing paint is chosen from the group of materials having at least two excited emissive levels in a Boltzmann equilibrium, then the temperature readings obtained from the luminescence decay time T and/or the temperature-dependent spectral distribution of the luminescence can be checked and validated with the temperature readings obtained from equation (9) of the TADA technology.

7. The Measurement of Surface Temperature and Air Pressure Distributions with a Single Luminophor It was shown in section 5.0 above that the use of alternating illumination with lights of two different sets of wavelengths $\lambda_1$ and $\lambda_v$ allows accurate temperature measurements regardless of thickness variations. It should be apparent that other inhomogeneities are also canceled out.

The determination of air pressure distributions in the presence of temperature or other physical variables affecting the photoluminescent paint can be effected by measuring the oxygen-dependent luminescence decay time of the photoluminescent material. This requires, if not a perfectly homogeneous paint, at least a calibration of the actual paint. This can be effected by applying as homogeneous a paint as practical (without very laborious and/or 'heroic' efforts), keeping the painted surface at a homogeneous temperature in an oxygen-free environment, and illuminating it with a light beam of wavelength or wavelengths $\lambda_1$ which is homogeneous over the tested area of the paint. Any luminescence intensity variations over the paint will be due to inhomogeneities on the paint itself. From these luminescence intensity variations one can determine the correction factors to be applied at each and all points.

In practice, the luminescence intensity variations over the painted area (which are generated not only by temperature and/or air pressure distributions but also by any present paint inhomogeneities present) are recorded as a luminescence image by digital cameras and computer-processed. The number of exposures depends, inter alia, on the nature of the paint used, and on whether the surface is stationary or moving rapidly.

The procedure and arrangement for measuring surface temperature and air pressure distributions follows clearly from the teachings of sections 3.0, 3.1 anf 5.0 above. A coating (paint) containing a photoluminescent material having an oxygen-sensitive luminescence decay time T is applied to the surface of interest. The coating has been calibrated as described in section 3.1 above. In a preferred embodiment the air pressure and temperature distributions are obtained as follows:

(1) The paint is excited with a short, intense pulse of light of wavelength or wavelengths $\lambda_1$ (which is absorbed by the photoluminescent material with little or no temperature dependence) and known intensity $P_1$. The pulse duration is preferably more than an order of magnitude shorter than about the average of the distributed decay times of the luminescence under the air pressures being measured, said average designated herein as $T_{av}$.

(2) At a pre-selected time t after the excitation light pulse has been extinguished, but beginning before a time of about $0.3T_{av}$, has elapsed, the first of two successive short time 'slices' of the time-decaying luminescence intensity distributions (images), each of duration $\Delta t$ shorter than $0.5T_{av}$, is focused on and processed by a digital video device, followed by the second time 'slice'. The relative luminescence intensities from each point at said two luminescence images give the value of T at each point on the illuminated paint.

(3) The luminescence spatial distribution of the first time 'slice' is saved and stored.

(4) Now the paint is excited with a short, intense pulse of light of wavelength or wavelengths $\lambda_v$ (the absorption of which by the photoluminescent material is substantially temperature-dependent), known intensity $P_1$, and the same duration as that of the light pulse of wavelength $\lambda_1$.

(5) At the same pre-selected time T after the excitation light pulse has been extinguished, a time 'slice' of the luminescence image generated by said pulse of light of wavelength or wavelengths $\lambda_v$, of the same duration $\Delta t$ as that of the first time "slice" of the luminescence excited by the light pulse of wavelength $\lambda_1$, is focused on and processed by the same or an identical digital video device.

(6) For each point on the photoluminescent paint, the relative luminescence signals generated by the excitation lights of wavelengths $\lambda_1$ and $\lambda_v$ and processed by the digital video device(s) define the temperature at that point according to equation (9) (section 2, supra). The temperature data for each point are applied to the T values obtained in step (2), thus providing a temperature compensation factor for converting each T value at each point on the paint surface to a true air pressure.

8. Temperature Measurement with Optical Probe Materials the Electronic Energy Levels of which are Shifted Under the Influence of Another Physical Parameter The preceding technical disclosures showed how temperature can be measured using probe materials whose energy levels are essentially unaffected by the physical parameter being measured. But, as stated above in the "BACKGROUND" section, electrical and/or magnetic fields can cause spectral shifts of one or more electronic energy levels of some temperature probe materials including semiconductors and rare earth-doped materials. Here we show how to measure temperature even when the excited electronic energy levels of the probe materials are being shifted by said electrical and/or magnetic fields or by any other physical field that can cause such spectral shifts, even when the extent of the shift is not readily known.

Consider, for example, a $Nd^{3+}$-doped probe material (among many suitable materials). In the absence of a perturbing field, the energy $E_s$ of the excited emissive level of the probe material which is excited by light of wavelength $\lambda_v$ is known, and said wavelength excites $Nd^{3+}$ ions occupying a thermally excited level with an energy of $E_v$ cm$^{-1}$ above the ground level. The value of this energy is the difference $(E_s-1/\lambda_v)$ cm$^{-1}$. When the probe is under a perturbing field, whether electric or magnetic (or both), the value of $E_v$ increases or decreases by the value $\delta E$, determined at least in part by the energy shift caused by the field on one of the energy levels involved in the absorption of the excitation light of said wavelength $\lambda_v$. At a temperature T, preferable between $(E_v/7k)$ and $(E_v/3k)$, the luminescence intensity generated by the absorption of said light follows the relation:

$$I=PK\phi \exp[-(E_v \pm \delta E)/kT] \tag{10}$$

where P is the power of the excitation light. This is essentially equation (8) modified by the uncertainty of $\pm \delta E$ caused by the perturbing field.

According to this invention one can measure the probe temperature without the need to know the value of $\delta E$. This can be done by exciting the probe successively with excitation lights of two wavelengths $\lambda_{v1}$ and $\lambda_{v2}$ within the same chosen absorption and luminescence excitation band. Said lights of wavelengths $\lambda_{v1}$ and $\lambda_{v2}$, of intensities $P_1$ and $P_2$, respectively, are further so chosen that they both excite $Nd^{3+}$ ions occupying thermally excited levels with energies of $(E_{v1} \pm \delta E)$ cm$^{-1}$ and $(E_{v2} \pm \delta E)$ cm$^{-1}$, respectively, above the ground level, and generate luminescence intensities $I_1$ and $I_2$, respectively, according to the relations:

$$I_1 = P_1 K \phi \exp[-(E_{v1} \pm \delta E)/kT] \quad (11)$$

and $$I_2 = P_2 K \phi \exp[-(E_{v2} \pm \delta E)/kT] \quad (12)$$

where K is a constant. Taking the ratio $(I_2/I_1)$ and solving for T leads to:

$$T = \Delta E_v / k . ln(I_2 P_1 / I_1 P_2) \quad (13)$$

where $\Delta E_v = (E_{v2} - E_{v1})$. Its value in units of cm$^{-1}$ is equal to $(1/\lambda_{v1} - 1/\lambda_{v2})$, so it is known and actually chosen by the person(s) doing the measurement. Note that $\delta E$ was canceled out, so it is not necessary to know its magnitude.

9. The Measurement of Temperature-Corrected Electrical Currents and/or Magnetic Fields There is a deeply felt need to remotely measure electrical currents in electrical power generation and distribution systems. Electrical sensing techniques are not suitable because of interference with the transmission of the signals by the high electrical fields in these systems. A great deal of effort has been underway at numerous laboratories to develop a suitable fiber optic measurement technique. Prior art fiber optic techniques make us of the Faraday effect, namely the rotation of plane polarized light (Faraday rotation) under the action of the magnetic field generated by the electrical current. In practice, an optical fiber having a core made of a Faraday rotator glass is coiled around a current-carrying conductor. The interrogating light is polarized by means of a first polarizing filter and injected into the fiber core at the fiber launch end. The current-generated magnetic field rotates the plane of polarization of the light propagating along the fiber core to a degree determined by the magnitude of the electrical current. In order to determine the degree of polarization, and hence the magnitude of the current, the light exiting from the fiber distal end is split into two beams. One of the beams is passed through a second polarizing filter orientated parallel to said first polarizing filter, and the other beam is passed through a third polarizing filter orientated perpendicular to said second polarizing filter. The relative intensities of the lights passing through said second and said third polarizing filters are an indicator of the degree of rotation of the plane of polarization of the interrogating light injected into said fiber core and, hence, of the magnitude of the electrical current.

Figure 4:
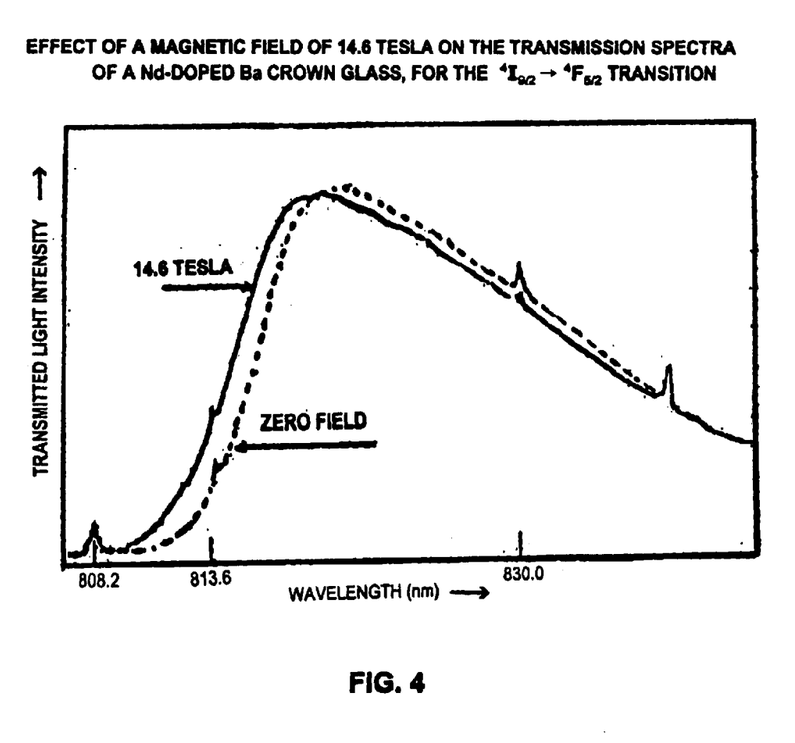
FIG. 4 shows the effect of an applied magnetic field of 14.6 Tesla on the light transmission at the long wavelength 'tail' of the $^4I_{9/2} \rightarrow {}^4I_{5/2}$ electronic transition of $Nd^{3+}$ in a Nd-doped barium crown glass at 4.2K.

It is also known that sufficiently strong magnetic fields, including those produced by high electrical currents generated in electrical power generation stations, can spectrally broaden or shift one or more absorption or photoluminescence bands of some materials doped with transition metal ions or rare earth ions. The effect is more easily observed in single crystalline materials, but can be sufficiently strong in some cases to be observed in disordered media like glasses. FIG. 4 shows such a spectral shift observed by the applicant in a Nd-doped barium crown glass at 4.2K, under a magnetic field of 14.6 Tesla, for the long wavelength 'tail' of the $^4I_{9/2} \rightarrow ^4I_{5/2}$ electronic optical transition of $Nd^{3+}$ (this effect was observed at the National Magnet Laboratory in 1984. The 'kinks' at the wavelengths of 808.2 nm, 813.6 nm and 830.0 nm are wavelength markers). Since this material is also photoluminescent, like most $Nd^{3+}$-doped inorganic transparent materials, the shift could be used for measuring high magnetic fields using this or a similar material as a probe. But the spectral shift at said 'tail' is also temperature-dependent, as in virtually all solid or liquid light-absorbing materials, and this cross sensitivity makes the optical measurement of the magnetic field-induced spectral shift unreliable, unless one could also measure any temperature changes independently of any changes produced by the magnetic field. Now, this is precisely what is taught in section 8, supra. Thus, this invention makes it possible to measure high electrical currents and magnetic fields using photoluminescent materials the spectral properties of which are appreciably modified by said high electrical currents or magnetic fields.

In one preferred procedure using a suitable instrument, the instrument vendor or the user would obtain a plot, at a given reference temperature, of the spectral shift (or the change of the photoluminescence intensity excited with light of a suitable wavelength) as a function of the strength of a magnetic field. For each of a number of magnetic field strengths, the instrument vendor or the user would plot the magnitude of the spectral shift (or the change of the photoluminescence intensity excited by light of a suitable wavelength) vs. temperature, using equation (13), in order to obtain the relevant temperature correction factors. Once these data are stored and made retrievable, the measurement of the magnetic field (or the electrical current) involves the steps of measuring both the temperature and the spectral shift generated by the electrical current or the magnetic field. Then the relevant temperature correction factor can be applied to the observed spectral shift or said change of the photoluminescence intensity, thus obtaining a reasonably accurate value of the magnetic field and/or the electrical current that generated that field.

10. The Measurement of Electrical Voltages and/or Electric Fields

It is well known that the light absorption and/or luminescence bands of some transition metal and/or rare earth ions in crystals or other media can be spectrally broadened or shifted by strong electric fields. This is generally known as a "Stark effect".

It is also well known that the optical absorption bands of semiconductors can be spectrally shifted to longer wavelengths under an applied electrical field. This phenomenon is widely known as the "Franz-Keldysh effect". Therefore, if a photoluminescent semiconductor is interrogated at the long wavelength tail of an optical absorption band, its absorption coefficient and, hence, its luminescence intensity will increase as a known function of the applied electric field and, hence, of an electrical voltage.

But such spectral shifts or broadenings can also be temperature-dependent, and this cross sensitivity has made unreliable the optical measurement, in the prior art, of electric fields by the Franz-Keldysh effect.

This invention, especially the teachings of section 8, supra, makes it possible to use the Franz-Keldysh effect, the Stark effect, or any other physical field which shifts the light absorption and/or the photo-luminescence spectral bands of photoluminescent materials, even under varying temperatures, without having to use another probe for the measurement of said varying temperatures.

A preferred procedure is essentially the same as that described above (section 9, supra) for the measurement of electrical currents and/or magnetic fields.

Since changes may be made in the foregoing disclosure without departing from the scope of the invention herein involved, it is intended that all matter contained in the above description and depicted in the accompanying drawings be construed in an illustrative and not in a limiting case.

I claim:

1. A method for measuring the temperature of an object or environment with a photoluminescent probe, comprising the steps of:
    a) providing a probe in thermal communication with said object or environment, said probe including a photoluminescent material so characterized that, when illuminated at any temperature within the temperature range of application of the method with a first excitation light of intensity $P_1$ and pre-selected wavelength or wavelengths $\lambda_1$, it emits a first luminescence light of intensity $I_1$, and when illuminated with a second excitation light of intensity $P_T$ and pre-selected wavelength or wavelengths $\lambda_v$, it emits a second luminescence light of intensity $I_T$ so related to the luminescence intensity $I_1$ that the ratio $(I_T.P_1/I_1.P_T)$ varies substantially in a known manner with varying temperature independently of any temperature-dependent changes in the luminescence efficiency of said photoluminescent material;
    b) illuminating said material with said first excitation light of said wavelength or wavelengths $\lambda_1$ and intensity $P_1$, thereby generating a first luminescence light emitted by the probe with said intensity $I_1$;
    c) directing a fraction of said intensity $I_1$ of said first luminescence light to photodetector means;
    d) illuminating said material, subsequently to its illumination with said first excitation light, with said second excitation light of an intensity $P_T$ and wavelength or wavelengths $\lambda_v$, thereby generating a second luminescence light emitted by the probe having an intensity $I_T$;
    e) directing a fraction of said intensity $I_T$ of said second luminescence light to photodetector means; and
    f) measuring the relative intensities of the luminescence lights generated by said first and said second excitation lights received by said photodetector means, said relative intensities being an indicator of the temperature being measured.

2. A method as claimed in claim 1 wherein the ratio $(I_T.P_1/I_1.P_T)$ increases substantially in a known manner with increasing temperature.

3. A method as claimed in claim 1 wherein said probe is attached to the distal end of an optical fiber light guide having a proximal end and a terminal end; said first and second excitation lights are injected into the optical fiber light guide at or near its proximal end, and said fractions of the intensities of said first and said second luminescence lights are directed by said optical fiber light guide to said photodetector means, said photodetector means being located near the proximal end of said optical fiber light guide.

4. A method as claimed in claim 1 and adapted to measure oxygen pressure in addition to temperature, wherein said photoluminescent material is additionally so characterized that, when excited with said excitation light of wavelength or wavelengths $\lambda_1$ at any temperature within the useable temperature range of application of the method, it emits a luminescence light with a normalized intensity, relative to the intensity of the excitation light of wavelength or wavelengths $\lambda_1$, which decreases in a known manner with increasing oxygen pressure, the method additionally comprising the step of measuring said normalized luminescence intensity, said intensity being an indicator of said oxygen pressure at the measured temperature.

5. A method as claimed in claim 1 and adapted to measure oxygen pressure in addition to temperature, wherein said photoluminescent material is additionally so characterized that, when excited with said excitation light of wavelength or wavelengths $\lambda_1$ at any temperature within the useable temperature range of application of the method, it emits a luminescence light having a decay time T which decreases in a known manner with increasing oxygen pressure, the method additionally comprising the steps of exciting said material with said pulsed or AC-modulated light and measuring said luminescence decay time, said decay time being an indicator of said oxygen pressure at the measured temperature.

6. A method as claimed in claim 4 wherein said probe is attached to the distal end of an optical fiber light guide having a proximal end and a terminal end; said excitation lights are injected into the optical fiber light guide at or near its proximal end, and said luminescence lights are directed by said optical fiber light guide to said photodetector means, said photodetector means being located near the proximal end of said optical fiber light guide.

7. A method as claimed in claim 4 wherein said photoluminescent material is comprised of a single luminophor.

8. An arrangement for measuring the temperature of an object or environment, comprising
    a) a probe in thermal communication with said object or environment, said probe including a photoluminescent material so characterized that, when illuminated at any temperature within the temperature range of application of the arrangement with a first excitation light of intensity $P_1$ and pre-selected wavelength or wavelengths $\lambda_1$, it emits a first luminescence light of intensity $I_1$, and when illuminated with a second excitation light of intensity $P_T$ and pre-selected wavelength or wavelengths $\lambda_v$, it emits a second luminescence light of intensity $I_T$, the relative responses of the luminescence intensities $I_T$ and $I_1$ to a temperature change being such that the ratio $(I_T.P_1/I_1.P_T)$ varies substantially in a known manner with increasing temperature;
    b) first light source means for illuminating said material with said first excitation light of said wavelength or wavelengths $\lambda_1$ and intensity $P_1$, and thus generating a first luminescence light emitted by the probe with said intensity $I_1$;
    c) second light source means for illuminating said material with said second excitation light of an intensity $P_T$ and wavelength or wavelengths $\lambda_v$, thereby generating a second luminescence light emitted by the probe having an intensity $I_T$;
    d) optical means for directing a fraction of said intensity $I_1$ of said first luminescence light to photodetector means;
    e) optical means for directing a fraction of said intensity $I_T$ of said second luminescence light to photodetector means; and
    f) photodetector and associated electronic means for measuring the relative intensities of the luminescence lights generated by said first and said second excitation lights received by said photodetector means, said relative intensities being an indicator of the temperature being measured.

9. An arrangement as claimed in claim 8 wherein said probe is attached to the distal end of an optical fiber light guide having a proximal end and a terminal end; said first and said second excitation light source means are configured to inject said first and said second excitation lights into the optical fiber light guide at or near its proximal end; said optical fiber light guide is provided with optical pathways for directing fractions of the intensities of said first and said second luminescence lights to said photodetector means, said photodetector means being located near the proximal end of said optical fiber light guide.

10. An arrangement as claimed in claim 8 wherein said probe is a coating applied to the surface of said object or part thereof.

11. An arrangement as claimed in claim 8 and adapted to measure oxygen pressure in addition to temperature, wherein said photoluminescent material is additionally so characterized that, when excited with said excitation light of wavelength or wavelengths $\lambda_1$ at any temperature within the useable temperature range of application of the method, it emits a luminescence light with a normalized intensity, relative to the intensity of the excitation light of wavelength or wavelengths $\lambda_1$, which decreases in a known manner with increasing oxygen pressure, the arrangement additionally comprising means for measuring said normalized luminescence intensity, said intensity being an indicator of said oxygen pressure at the measured temperature.

12. An arrangement as claimed in claim 11 wherein said probe is attached to the distal end of an optical fiber light guide having a proximal end and a terminal end; said excitation lights are injected into the optical fiber light guide at or near its proximal end, and said luminescence lights are directed by said optical fiber light guide to photodetector means, said photodetector means being located near the proximal end of said optical fiber light guide.

13. An arrangement as claimed in claim 8 and adapted to measure oxygen pressure in addition to temperature, wherein said photoluminescent material is additionally so characterized that, when excited with a pulsed or AC-modulated light of wavelength or wavelengths $\lambda_1$ at any temperature within the useable temperature range of application of the arrangement, it emits a luminescence light with a decay time T which decreases in a known manner with increasing oxygen pressure, the arrangement additionally comprising the light source means for exciting the luminescence of said material with said pulsed or AC-modulated light and for measuring said luminescence decay time, said decay time being an indicator of said oxygen pressure at the measured temperature.

14. An arrangement as claimed in claim 13 wherein said probe is attached to the distal end of an optical fiber light guide having a proximal end and a terminal end; said first and said second excitation light source means and said pulsed or AC-modulated light source means are configured to inject into the optical fiber light guide at or near its proximal end, and said luminescence lights are directed by said optical fiber light guide to said photodetector means, said photodetector means being located near the proximal end of said optical fiber light guide.

15. A method for measuring temperature with a photoluminescent probe, comprising the steps of:

a) providing a probe in thermal communication with said object or environment, said probe including a photoluminescent material so characterized that, when illuminated at any temperature within the temperature range of application of the method with a first excitation light of intensity $P_1$ and wavelength or wavelengths $\lambda_{v1}$, it emits a first luminescence light of intensity $I_1$, and when illuminated with a second excitation light of intensity $P_2$ and pre-selected wavelength or wavelengths $\lambda_{v2}$, it emits a second luminescence light of intensity $I_T$ so related to the luminescence intensity $I_1$ that the ratio $(I_2.P_1/I_1.P_2)$ varies substantially in a known manner with varying temperature independently of any temperature-dependent changes in the luminescence efficiency of said photoluminescent material, the wavelengths $\lambda_{v1}$ and $\lambda_{v2}$ being within the same chosen absorption and luminescence excitation band and so chosen that each of said excitation lights excites the luminescence of molecules or ions of said material occupying a thermally excited level, the energy level of the molecules or ions excited by light of wavelengths $\lambda_{v1}$ being measurably different from the energy level of the molecules or ions excited by light of wavelengths $\lambda_{v2}$;

b) illuminating said material with said first excitation light of said wavelength or wavelengths $\lambda_{v1}$ and intensity $P_1$, thereby generating a first luminescence light emitted by the probe with said intensity $I_1$;

c) directing a fraction of said intensity $I_1$ of said first luminescence light to photodetector means;

d) illuminating said material, subsequently to its illumination with said first excitation light, with said second excitation light of an intensity $P_2$ and wavelength or wavelengths $\lambda_{v2}$, thereby generating a second luminescence light emitted by the probe having an intensity $I_2$;

e) directing a fraction of said intensity $I_T$ of said second luminescence light to photodetector means; and f) measuring the relative intensities of the luminescence lights generated by said first and said second excitation lights received by said photodetector means, said relative intensities being an indicator of the temperature being measured.

16. A method as claimed in claim 15 and adapted to measure a second physical parameter in addition to temperature, said second physical parameter chosen from the group comprising an electrical current, a magnetic field and an electrical field or voltage.

* * * * *